United States Patent
Toy et al.

(10) Patent No.: US 8,442,643 B2
(45) Date of Patent: May 14, 2013

(54) MEDICAL DEVICE PROGRAMMER WITH REDUCED-NOISE POWER SUPPLY

(75) Inventors: Alex C. Toy, North St. Paul, MN (US); John W. Forsberg, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 2296 days.

(21) Appl. No.: 10/693,012

(22) Filed: Oct. 24, 2003

(65) Prior Publication Data
US 2005/0075690 A1    Apr. 7, 2005

Related U.S. Application Data

(60) Provisional application No. 60/508,511, filed on Oct. 2, 2003.

(51) Int. Cl.
*A61N 1/378* (2006.01)

(52) U.S. Cl.
USPC .......................................................... 607/60

(58) Field of Classification Search ................... 607/32, 607/903, 128, 60
See application file for complete search history.

(56) References Cited

U.S. PATENT DOCUMENTS

| | | | |
|---|---|---|---|
| 2,144,310 A | 1/1939 | Hyland | |
| 2,147,148 A | 2/1939 | Charrier | |
| 2,203,517 A | 6/1940 | Beggs | |
| 2,273,955 A | 2/1942 | Grimditch | |
| 2,292,182 A | 8/1942 | Van Billiard | |
| 2,343,306 A | 3/1944 | Lear | |
| 2,621,004 A | 12/1952 | Polydoroff | |
| 3,495,264 A | 2/1970 | Spears | |
| 3,683,389 A | 8/1972 | Hollis | |
| 3,796,221 A | 3/1974 | Hagfors | |
| 4,066,086 A * | 1/1978 | Alferness et al. ............... 607/59 |
| 4,201,965 A | 5/1980 | Onyshkevych | |
| 4,408,608 A * | 10/1983 | Daly et al. ..................... 607/57 |
| 4,432,360 A | 2/1984 | Mumford et al. | |
| 4,550,370 A * | 10/1985 | Baker ............................. 607/31 |
| 4,586,508 A | 5/1986 | Batina et al. | |
| 4,601,557 A | 7/1986 | Bogle et al. | |
| 4,690,144 A | 9/1987 | Rise et al. | |
| 5,833,623 A | 11/1998 | Mann et al. | |
| 5,903,138 A | 5/1999 | Hwang et al. | |
| 5,967,986 A | 10/1999 | Cimochowski et al. | |

(Continued)

FOREIGN PATENT DOCUMENTS

| WO | WO 03/008014 | 1/2003 |
|---|---|---|
| WO | WO 03/037430 | 5/2003 |
| WO | WO 03/040986 | 5/2003 |

OTHER PUBLICATIONS

Notification of Transmittal of the International Preliminary Report on Patentability dated Apr. 5, 2005, International Application No. PCT/US2004/002482.

(Continued)

*Primary Examiner* — Joseph Stoklosa
(74) *Attorney, Agent, or Firm* — Shumaker & Sieffert, P.A.

(57) ABSTRACT

A programmer for a medical device, such as a neurostimulator, includes a reduced-noise power supply that converts dc power provided by a battery source to power for components within the programmer. The power supply includes a pulse-skipping dc-dc boost converter. The programmer provides an input circuit for selectively inhibiting pulse-skipping to reduce switching noise that could otherwise undermine wireless telemetry performance between the programmer and a medical device.

32 Claims, 6 Drawing Sheets

U.S. PATENT DOCUMENTS

| | | | |
|---|---|---|---|
| 6,055,168 | A | 4/2000 | Kotowski et al. |
| 6,073,033 | A | 6/2000 | Campo |
| 6,162,180 | A | 12/2000 | Miesel et al. |
| 6,219,255 | B1 | 4/2001 | Teshome |
| 6,249,703 | B1 | 6/2001 | Stanton et al. |
| 6,263,246 | B1 | 7/2001 | Goedeke et al. |
| 6,366,070 | B1 | 4/2002 | Cooke et al. |
| D459,814 | S | 7/2002 | Lee et al. |
| 6,418,346 | B1 | 7/2002 | Nelson et al. |
| 6,469,914 | B1 * | 10/2002 | Hwang et al. ............. 363/21.01 |
| 6,516,227 | B1 | 2/2003 | Meadows et al. |
| 6,556,871 | B2 | 4/2003 | Schmitt et al. |
| 6,561,975 | B1 | 5/2003 | Pool et al. |
| 6,614,664 | B2 | 9/2003 | Lee |
| 6,622,048 | B1 | 9/2003 | Mann et al. |
| 6,631,296 | B1 | 10/2003 | Parramon et al. |
| 6,678,563 | B2 | 1/2004 | Fang et al. |
| 6,687,538 | B1 | 2/2004 | Hrdlika et al. |
| 6,693,015 | B2 | 2/2004 | Carstensen |
| 6,704,600 | B2 | 3/2004 | Daum |
| 6,731,986 | B2 | 5/2004 | Mann |
| 6,735,474 | B1 | 5/2004 | Loeb et al. |
| 6,754,527 | B2 | 6/2004 | Stroebel et al. |
| 6,804,558 | B2 | 10/2004 | Haller et al. |
| 7,177,698 | B2 * | 2/2007 | Klosterman et al. ............ 607/60 |
| 2002/0052539 | A1 | 5/2002 | Haller et al. |
| 2002/0055761 | A1 | 5/2002 | Mann et al. |
| 2002/0074975 | A1 | 6/2002 | Culpepper et al. |
| 2002/0123673 | A1 | 9/2002 | Webb et al. |
| 2003/0036783 | A1 | 2/2003 | Bauhahn et al. |
| 2003/0065308 | A1 | 4/2003 | Lebel et al. |
| 2003/0114899 | A1 | 6/2003 | Woods et al. |
| 2003/0139782 | A1 | 7/2003 | Duncan et al. |
| 2003/0174066 | A1 | 9/2003 | Goetz et al. |
| 2003/0174069 | A1 | 9/2003 | Goetz et al. |
| 2003/0176906 | A1 | 9/2003 | Lee |
| 2003/0177031 | A1 | 9/2003 | Malek |
| 2003/0195581 | A1 * | 10/2003 | Meadows et al. ............... 607/29 |
| 2003/0204223 | A1 | 10/2003 | Leinders et al. |
| 2003/0229383 | A1 | 12/2003 | Whitehurst et al. |
| 2004/0064166 | A1 | 4/2004 | Thompson et al. |
| 2004/0098068 | A1 * | 5/2004 | Carbunaru et al. ............ 607/60 |
| 2004/0199212 | A1 | 10/2004 | Fischell et al. |
| 2005/0075684 | A1 | 4/2005 | Phillips et al. |
| 2005/0075685 | A1 | 4/2005 | Forsberg et al. |
| 2005/0075686 | A1 | 4/2005 | Phillips et al. |
| 2005/0075687 | A1 | 4/2005 | Phillips et al. |
| 2005/0075688 | A1 | 4/2005 | Toy et al. |
| 2005/0075689 | A1 | 4/2005 | Toy et al. |
| 2005/0075691 | A1 | 4/2005 | Phillips et al. |
| 2005/0075692 | A1 | 4/2005 | Schommer et al. |

OTHER PUBLICATIONS

Advanced Neuromodulation Systems New Rapid Programmer, 2003.

ANS' New Palm-Sized Programmer Provides Quick, Convenient Management of Pain Therapy, 2003.

Lin et al., "A Wireless PDA-Based Physiological Monitoring System for Patient Transport," IEEE Transactions on Information Technology in Biomedicine, vol. 8, No. 4, pp. 439-447, Dec. 2004.

* cited by examiner

MEDICAL DEVICE PROGRAMMER WITH REDUCED-NOISE POWER SUPPLY

This application claims priority from U.S. provisional application Ser. No. 60/508,511, filed Oct. 2, 2003, the entire content of which is incorporated herein by reference.

TECHNICAL FIELD

The invention relates to medical devices and, more particularly, to programmers for medical devices.

BACKGROUND

Implantable medical devices are used to deliver therapy to patients to treat a variety of symptoms or conditions. An implantable neurostimulator, for example, may treat symptoms or conditions such as chronic pain, tremor, Parkinson's disease, epilepsy, incontinence, or gastroparesis. The implantable medical device delivers neurostimulation therapy via one or more leads that include electrodes located proximate to the spinal cord, pelvic nerves, or stomach, or within the brain of a patient. In general, the implantable medical device delivers neurostimulation therapy in the form of electrical pulses.

A clinician selects values for a number of programmable parameters in order to define the therapy to be delivered to a patient. With a neurostimulator, for example, the clinician may select an amplitude, which may be a current or voltage amplitude, and pulse width for a stimulation waveform to be delivered to the patient, as well as a rate at which the pulses are to be delivered to the patient. In addition, the clinician also selects particular electrodes within an electrode set to be used to deliver the pulses, and the polarities of the selected electrodes.

The clinician uses a clinician programmer to program the parameters into the implantable medical device. The implantable medical device may store multiple programs, however, which may be selected by the patient using a patient programmer. The patient may select different programs to modify therapy delivered by the implantable medical devices, e.g., to achieve greater pain relief. Different programs may be appropriate for different times of day or different physical activities or postures.

The patient programmer communicates with the implantable medical device to modify programs using radio frequency (RF) telemetry. For this reason, the patient programmer includes an antenna for placement relative to the patient's body at a position near the implantable medical device. The patient programmer is typically designed as a mobile device that may be carried by the patient throughout the course of the day. For example, the patient programmer may be a handheld device, and typically is powered by batteries within the device.

SUMMARY

In general, the invention is directed to a programmer for a medical device such as an implantable medical device, e.g., an implantable neurostimulator. In accordance with the invention, the programmer includes a reduced-noise power supply that converts dc power provided by a battery source to power for components within the programmer. The power supply includes a pulse-skipping dc-dc boost converter. The programmer provides an input circuit for selectively inhibiting pulse-skipping to reduce switching noise that could otherwise undermine wireless telemetry performance between the programmer and an implanted medical device.

In one embodiment, the invention provides a programmer for an implantable medical device, the programmer comprising a wireless telemetry circuit to communicate with the implantable medical device, a pulse-skipping boost converter to convert a battery voltage to an operating voltage for the programmer, and a control circuit to inhibit pulse skipping by the boost converter based on a level of the battery voltage.

In another embodiment, the invention provides a method for controlling a power supply in a programmer for an implantable medical device, the method comprising applying a battery voltage to a pulse-skipping boost converter to convert the battery voltage to an operating voltage for the programmer, and inhibiting pulse skipping by the boost converter based on a level of the battery voltage.

In an added embodiment, the invention provides a system for controlling a power supply in a programmer for an implantable medical device, the system comprising means for applying a battery voltage to a pulse-skipping boost converter to convert the battery voltage to an operating voltage for the programmer, and means for inhibiting pulse skipping by the boost converter based on a level of the battery voltage.

The invention may provide a number of advantages. By inhibiting pulse skipping, a programmer in accordance with the invention can take advantage of conventional boost converter technology while reducing undesirable noise associated with such technology. In this manner, the programmer can be powered by common battery cells, such as AAA cells, and incorporate low-cost boost converter technology, while reducing adverse impacts on wireless telemetry performance. Accordingly, the battery-powered programmer is able to communicate more effectively with the implantable medical device, ensuring proper communication of programs and changes in device settings, and facilitating proper interrogation of the device.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
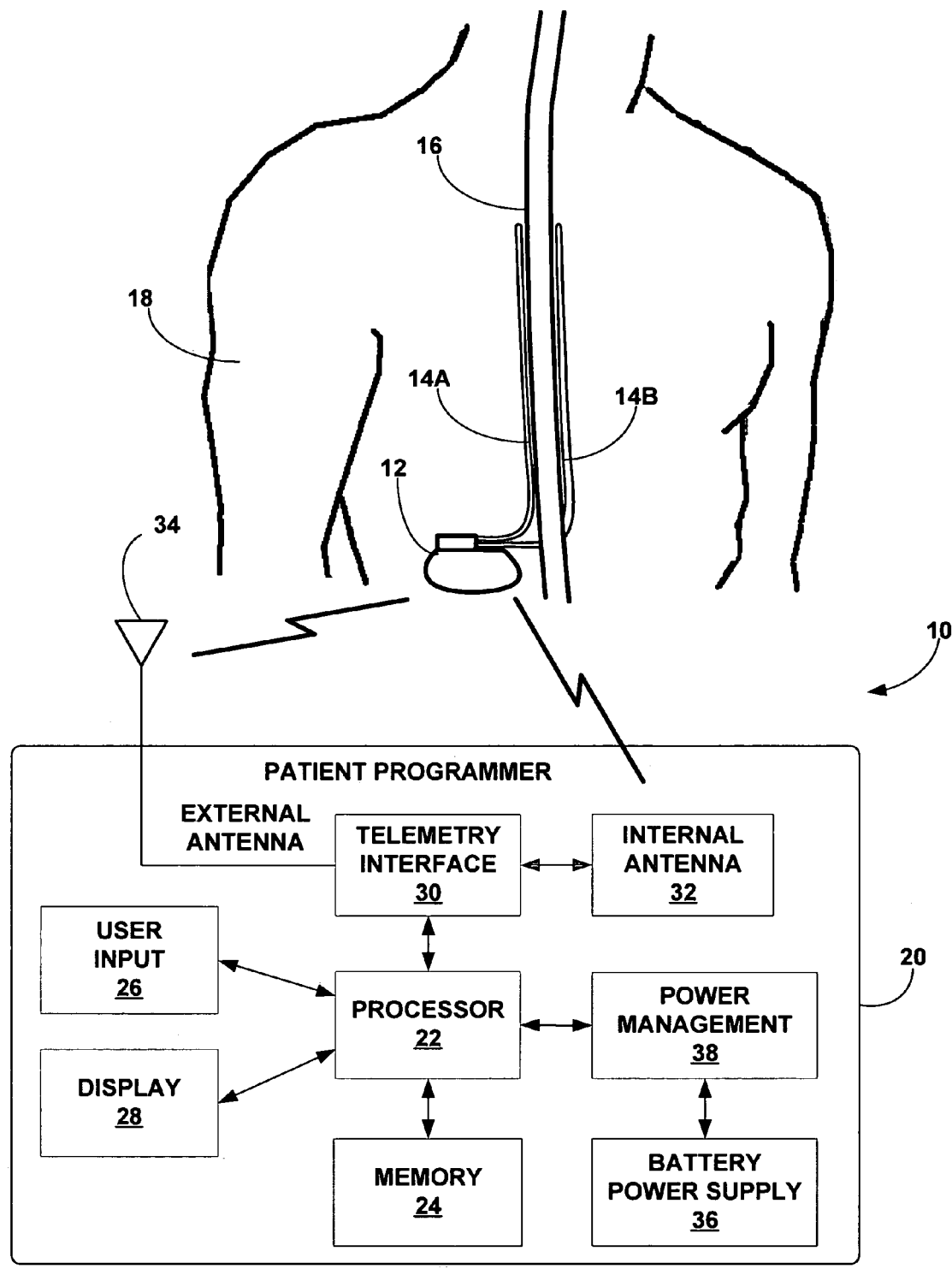
FIG. 1 is a conceptual diagram illustrating communication between a programmer and an implantable medical device.

FIG. 1 is a conceptual diagram illustrating a system 10 for programming an implantable medical device (IMD) 12 to deliver therapy to a patient 18. In some embodiments, IMD 12 may deliver neurostimulation therapy to patient 18. IMD 12 may be an implantable pulse generator, and may deliver neurostimulation therapy to patient 18 in the form of electrical pulses.

A programmer 20 communicates with IMD 12 by wireless telemetry to download programs, change device settings, and interrogate the IMD for status information. Programmer 20 may be useful with implantable medical devices, as well as external, non-implanted medical devices. As will be described, programmer 20 includes a reduced-noise power supply that converts dc power provided by a battery source to power for components within the programmer.

The reduced-noise power supply includes a pulse-skipping dc-dc boost converter. An input circuit in programmer 20 selectively inhibits pulse-skipping to reduce switching noise that could otherwise undermine wireless telemetry performance between the programmer and an implanted medical device.

As further shown in FIG. 1, IMD 12 delivers neurostimulation therapy to patient 18 via leads 14A and 14B (collectively "leads 14"). An IMD 12 that delivers neurostimulation therapy is illustrated for purposes of example. Implanted leads 14, as shown in FIG. 1, may be implanted proximate to the spinal cord 16 of patient 18. IMD 12 delivers spinal cord stimulation (SCS) therapy to patient 18 via leads 14. Spinal cord stimulation may be selected to reduce pain experienced by patient 18.

The invention is not limited to the configuration of leads 14 shown in FIG. 1, however, or the delivery of SCS therapy. For example, one or more leads 14 may extend from IMD 12 to the brain (not shown) of patient 18, and IMD 1412 may deliver deep brain stimulation (DBS) therapy to patient 18 to, for example, treat tremor or epilepsy. As further examples, one or more leads 14 may be implanted proximate to the pelvic nerves (not shown) or stomach (not shown), and IMD 12 may deliver neurostimulation therapy to treat incontinence or gastroparesis.

IMD 12 delivers neurostimulation therapy to patient 18 according to one or more neurostimulation therapy programs. A neurostimulation therapy program may include values for a number of parameters, and the parameter values define the neurostimulation therapy delivered according to that program. In embodiments where IMD 12 delivers neurostimulation therapy in the form of electrical pulses, the parameters may include pulse voltage or current amplitudes, pulse widths, pulse rates, and the like. Further, each of leads 14 includes electrodes (not shown), and the parameters for a program may include information identifying which electrodes have been selected for delivery of pulses according to the program, and the polarities of the selected electrodes.

System 10 also includes programmer 20, which may be a clinician programmer or patient programmer. Programmer 20 may be a handheld computing device. In the example of FIG. 1, programmer 20 is a patient programmer that may be carried by a patient throughout his daily routine to control programs and device settings within IMD 12. In some embodiments, programmer 20 may be used to program and interrogate non-implanted medical devices. As shown in FIG. 1, programmer 20 includes a processor 22, which may execute instructions stored in memory 24 to control functions performed by the patient programmer. Processor 22 may include a microprocessor, a controller, a DSP, an ASIC, an FPGA, discrete logic circuitry, or the like.

Programmer 20 further includes a display 28, such as an LCD or LED display, to display information to a user. Programmer 20 may also include a user input device 26, which may be used by a user to interact with programmer 20. In some embodiments, display 28 may be a touch screen display, and a user may interact with programmer 20 via display 28. A user may also interact with programmer 20 using peripheral pointing devices, such as a stylus or mouse. User input device 26 take the form of an alphanumeric keypad or a reduced set of keys associated with particular functions.

Processor 22 drives display electronics associated with display 28 to present status information and other data to patient 18. In addition, processor 22 receives user input entered by a user via user input 26 to control various operations performed by patient programmer 20. Processor 22 also controls a telemetry interface 30 to transmit and receive information, such as instructions and status information. In particular, telemetry interface 30 drives one or both of an internal antenna 32 and an external antenna 34 to transmit instructions to IMD 12. In addition, telemetry interface 30 processes signals received by internal antenna 32 and external antenna 34 from IMD 12. Internal antenna 32 is mounted within a housing associated with patient programmer 20, whereas external antenna 34 extends outward from patient programmer 20 via an antenna cable.

Patient 18 carries patient programmer 20 and uses the patient programmer to program neurostimulation therapy for the patient throughout the course of the patient's day. In the interest of portability, patient programmer 20 further includes a battery power supply 36 and a power management module 38, which will be described in greater detail below. Patient 18 may use programmer 20 to select different programs or modify parameter settings, such as amplitude, rate, electrode configuration, and the like to enhance therapeutic effects. Program or parameter changes may be appropriate for changes in physical activities, postures, time of day, or other events. Different programs or parameters may have different results in terms of symptom relief, coverage area relative to symptom area, and side effects.

A clinician programmer (not shown) may be used by a clinician to create neurostimulation therapy programs and load the programs either into memory associated with IMD 12 or patient programmer 20. Hence, in some embodiments, patient programmer 20 may be configured to download programs stored in memory associated with the patient programmer to IMD 12 to initiate new programs or modify existing programs. In other embodiments, however, patient programmer 20 merely communicates instructions to IMD 12 to select different programs or parameters settings from memory in the IMD. Memory 24 of patient programmer 20 may include a nonvolatile form of read-only memory (ROM), such as flash memory, FPGA, CPLD, or the like, and may store application software, device parameters, use data, diagnostic data, and other software related information. Read-only memory contents are retained without application of power. Memory 24 also may include random access memory (RAM) for execution of instructions by processor 22.

In order to modify programs and parameter settings and otherwise control IMD 12, patient programmer 20 communicates with IMD 12 via wireless telemetry techniques. For example, programmer 20 may communicate with IMD 12 via RF telemetry. In this manner, patient programmer 20 is used by patient 18 to control the delivery of neurostimulation therapy by IMD 14. For telemetry with IMD 12, patient programmer 20 may use either internal antenna 32 or external antenna 34 on a selective basis External antenna 34 may be attached to the patient programmer 20 via a cable, and many include an RF telemetry head for placement on the patient's body at a position near IMD 12. Internal antenna 32 is mounted within or on the housing of patient programmer 20, and may have a structure designed for performance and compactness. In addition, internal antenna 32 may facilitate programming of the IMD 12 by simply placing the patient programmer 20 on the patient's body at a position near the implanted medical device, thereby promoting patient convenience.

Display 28 and associated display electronic can produce significant electrical interference capable of degrading the performance of internal antenna 32 during telemetry sessions. The electrical interface may be particularly troublesome due to the relatively close proximity of internal antenna 32 to display 28 within the housing of patient programmer 20. For this reason, processor 22 or other control circuitry within patient programmer 20 may be configured to selectively disable, i.e., turn off, display 28 and associated display electronics during RF telemetry with internal antenna 32 to promote more reliable communication. For example, display 28 and display electronics may be temporarily disabled during reception of RF signals, transmission of RF signals, or both, by internal antenna 32.

In this manner, patient programmer 20 selectively controls the display 28 and display electronics to reduce electrical interference. Processor 22 then enables the display 28 and display electronics upon completion of telemetry using internal antenna 32. In some embodiments, patient programmer 20 may control display 28 to display information at a lower intensity, rather than turning off the display. When use of an external antenna 34 is detected, processor 22 may enable display 28, as interference may be less of a concern for the external antenna, which extends away from patient programmer 20 via a cable.

Another potential source of electrical interference is power management module 38. As will be described, power management module 38 includes a dc-dc boost converter that converts battery voltage from battery power supply 36 to operating voltage to power various components within programmer 20. The boost converter incorporates a pulse skipping feature, however, that can result in substantial switching noise. The noise can undermine the performance of telemetry interface 30, particularly when internal antenna 32 is used. For example, internal antenna 32 may be placed in close proximity to battery power supply 36 and power management module 38 within a housing associated with programmer.

The dc-dc boost convert design may have a fixed-frequency switching mode with a switching frequency that can be pre-selected by the circuit designer. The fixed switching frequency may be selected to minimize the effects of noise generated by the switching circuitry. When the input voltage to the boost converter is close to the output voltage of the boost converter, and there is a light current load on the output of the converter, the boost converter stops switching for brief periods of time to allow an output capacitor to discharge to a voltage defined by a feedback circuit. This feature is often referred to as "pulse-skipping," and can cause substantial electrical interference.

The switching noise caused by pulse skipping can be especially troublesome when new, i.e., "fresh," batteries are installed in programmer 20. Batteries will tend to carry a higher voltage when they are new, making the input voltage to the boost converter closer the output voltage. If the output voltage of the boost converter is approximately 3.3. volts, for example, two new AAA alkaline batteries may supply an input voltage as high as approximately 3.2 volts. Thus, the boost converter is more likely to undertake frequent pulse skipping when the batteries are new. Other types of battery cells may present similar issues, such as AA, C and D batteries.

In accordance with the invention, programmer 20 monitors the level of the battery voltage and inhibits pulse skipping based on the battery voltage. For example, programmer 20 may compare the monitored battery voltage to a threshold voltage and, if the battery voltage exceeds the threshold voltage, inhibit pulse skipping. In some embodiments, the threshold voltage may be on the order of approximately 2.4 to 2.6 volts. Hence, the threshold voltage may be effective in detecting the presence of new batteries, and continue to indicate a detection for pulse skipping as the batteries deplete to the threshold voltage. After the battery or batteries have dropped below the threshold voltage, pulse skipping is no longer inhibited, and is less likely to be raise performance issues given the reduced input voltage. To inhibit pulse skipping, programmer 20 may turn OFF a transistor, such as a MOSFET, that transmits the battery voltage to the boost converter. In this manner, the battery voltage is decreased by a diode drop created by the body diode in the MOSFET, thereby reducing the input voltage to the boost converter to inhibit pulse skipping.

Figure 2:
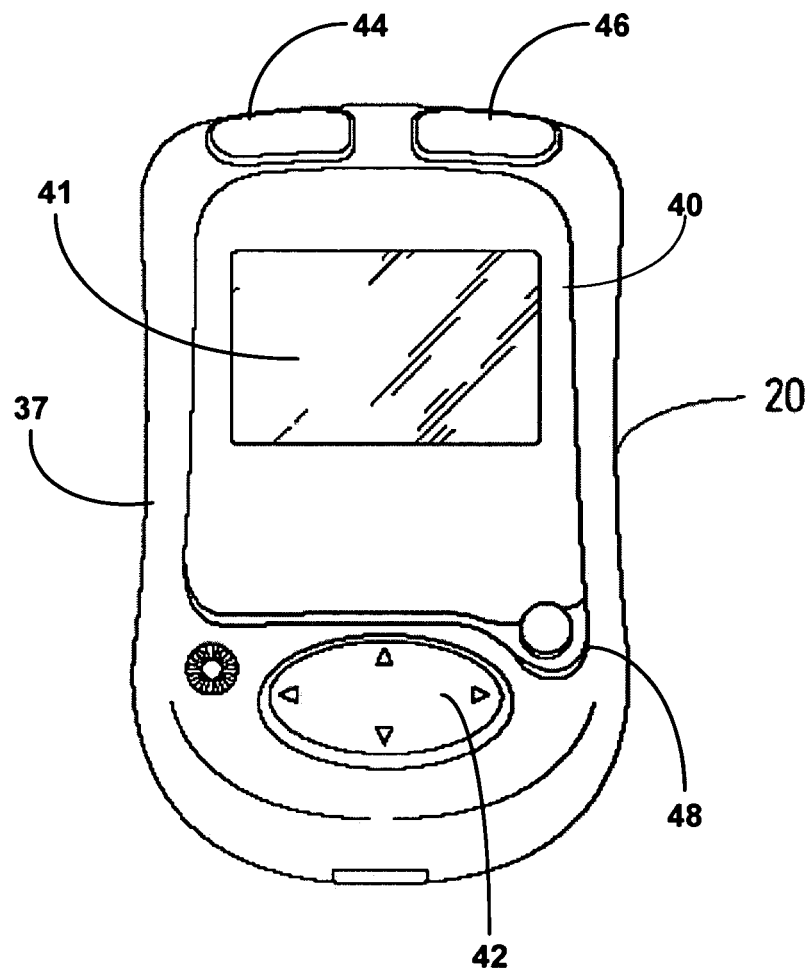
FIG. 2 is a front view of an exemplary housing for a programmer.

FIG. 2 is a front view of an exemplary housing for programmer 20. As shown in FIG. 2, patient programmer 20 includes a housing 37. Housing 37 may be formed of molded plastic and may include a lens cover faceplate 40 with a transparent display section 41 that exposes display 28. Faceplate 40 may be formed of a clear plastic material. Housing 37 contains various components of programmer 20, as depicted in FIG. 1. In particular, housing 37 may contain appropriate electronics for implementation of processor 22, user input device 26, display 28, memory 24, power management module 38, telemetry interface 30 and internal antenna 32. Housing 37 may include an access door for insertion of batteries into programmer 20 to form battery power supply 36.

As further shown in FIG. 2, housing 37 may include a variety of input buttons 42, 44, 46, 48, which form part of user input device 26 of FIG. 1. In the example of FIG. 2, buttons 44, 46 are minus and plus buttons, respectively, that may permit patient 18 to decrease and increase values of neurostimulation parameter settings. In particular, buttons 52, 54 may permit patient 18 to quickly increase and decrease the amplitude of stimulation being delivered by IMD 12. Button 48 is an on/off button that turns power on and off, and turns backlighting on and off. Button 42 is a four-way (up, down, left, right) rocker switch that permits navigation through items presented on display 28. Buttons 42, 44, 46, 48 may be devoted to a variety of functions such as activation of stimulation, deactivation of stimulation, and interrogation of IMD 12 to check device status.

Figure 3:
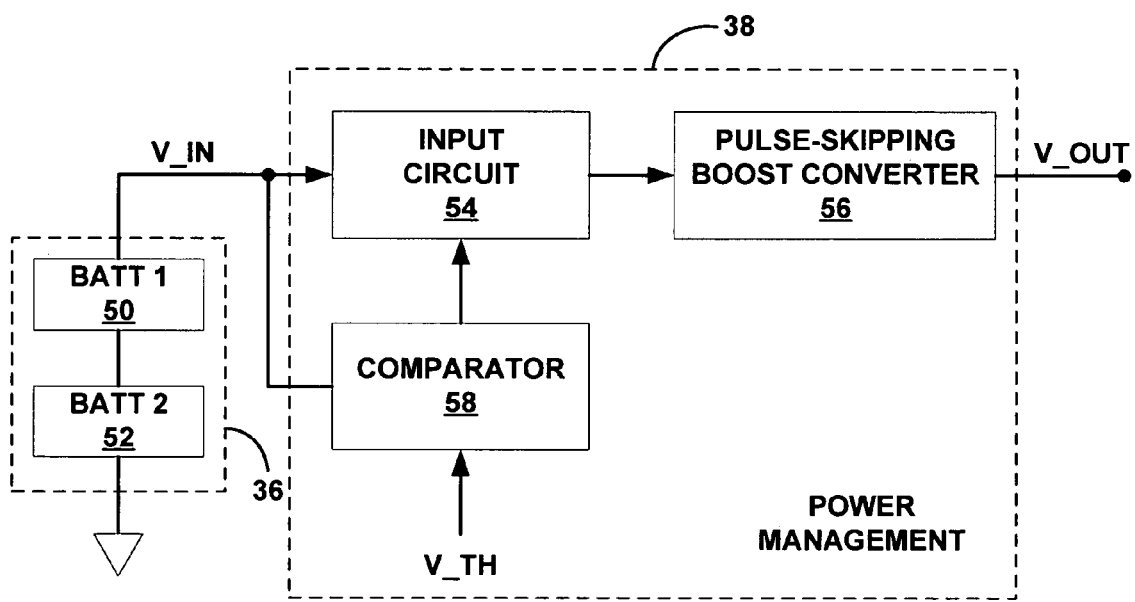
FIG. 3 is a block diagram illustrating a power management module for a programmer.

FIG. 3 is a block diagram illustrating a power management module 38 for a programmer 20. As shown in FIG. 3, power management module 38 receives an input voltage V_IN from battery power supply 36. Battery power supply 36 may include one or more batteries. In the example of FIG. 3, battery power supply 36 includes two batteries 50, 52 coupled in series.

Batteries 50, 52 may be realized by 1.5 volt AAA batteries. In series, the 1.5 volt AAA batteries produce a voltage V_IN of 3.0 volts. When the AAA batteries are new and "fresh," however, they may exhibit a higher voltage, such as approximately 1.6 to 1.7 volts per battery cell. In this case, input voltage V_IN may be on the order of 3.0 to 3.4 volts. If the input voltage V_IN is too high, the boost converter may enter the pulse skipping mode more frequently, which may create substantial switching noise that can undermine telemetry performance via telemetry interface 30.

Power management module 38, in accordance with the invention, provides circuitry for inhibiting pulse skipping under circumstances in which pulse skipping is caused generally by an excessive level of V_IN generated by battery power supply 36. As shown in FIG. 3, power management module 38 may include an input circuit 54, a pulse-skipping boost converter 56, and a comparator 58. Comparator 58 compares the input voltage level VIN to a threshold voltage level V_TH. Input circuit 54 reduces the input voltage level V_IN for application to boost converter 56 when comparator 58 indicates that the input voltage level V_IN exceeds the threshold voltage V_TH.

Comparator 58 may be implemented by analog comparator circuitry or digitally within processor 22. Input circuit 54, as will be described, may include a transistor such as a MOSFET that transmits the input voltage V_IN to boost converter 56. Boost converter 56 may be a conventional, commercially available boost converter circuit configured to provide pulse skipping. Upon determining that input voltage V_IN exceeds threshold voltage V_TH, as indicated by comparator 58, input circuit 54 reduces the level of V_IN prior to application to boost converter 56. In this manner, boost converter 56 operates on a reduced input voltage and is less likely to enter the pulse skipping mode, reducing the amount of noise in programmer 20 and avoiding adverse effects on telemetry performance.

Figure 4:
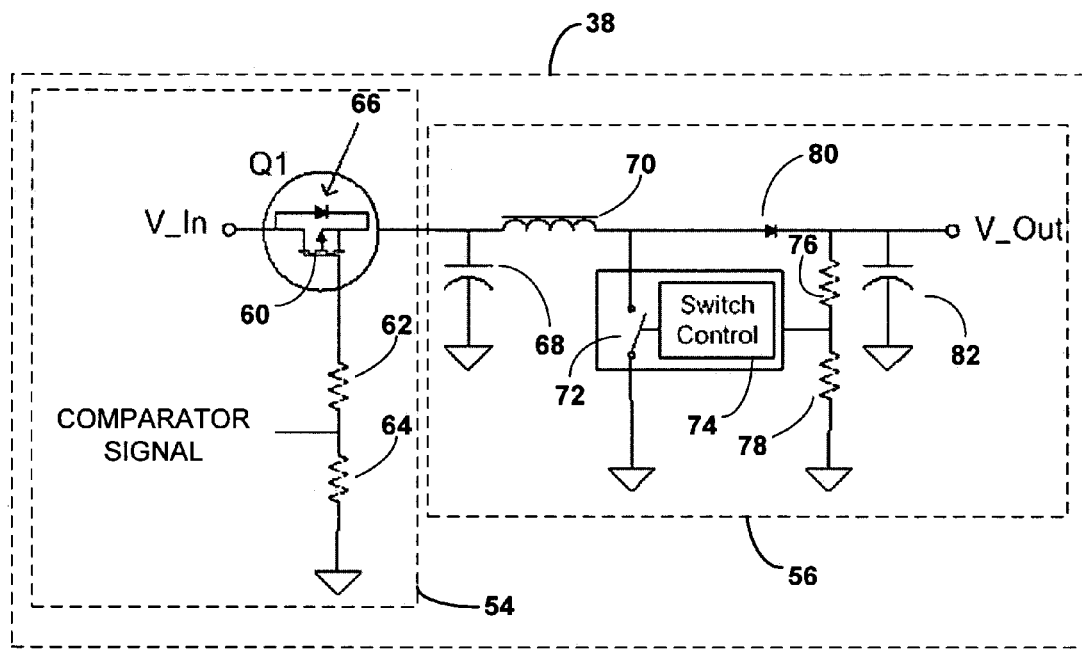
FIG. 4 is a circuit diagram illustrating the power management circuit of FIG. 3 in greater detail.

FIG. 4 is a circuit diagram illustrating power management module 38 of FIG. 4 in greater detail. As shown in FIG. 4, boost converter 56 may include conventional boost converter components, such as an input inductor 70 and capacitor 72 to set the operating frequency of the boost converter, a rectification diode 80, and an output capacitor 82. Output capacitor 82 charges to store the rectified output of diode 80 to produce a dc operating voltage V_OUT. If twdAAA batteries are used, for example, the operating voltage range may be on the order of approximately 2.2 to 3.2 volts.

In the event the output voltage V_OUT on capacitor 82 is too high, a switch 72 forming part of the pulse skipping circuitry decouples diode 80 and capacitor 82 from the input voltage provided by inductor 70 and capacitor 68. For example, boost converter 56 may include a resistor divider provided by resistors 76, 78. A switch control sensor 74 senses the voltage on resistor 78, and compares the voltage to a reference voltage. If the voltage on resistor 78 exceeds the reference voltage, switch control sensor 74 closes switch 72 to disable the boost converter. Switch control sensor 74 may be configured to close the switch 72 for one or more cycles, i.e., pulses, thereby resulting in pulse skipping. Switch 72 may be closed for a single cycle, or until the sensed voltage at resistor 78 drops below the reference voltage.

If the input voltage V_IN is too high, the output voltage on capacitor 82 in boost converter 56 will tend to be too high, resulting in excessive pulse skipping and associated electrical noise. To avoid excessive pulse skipping, particularly when new batteries are placed in programmer 20, input circuit provides a transistor such as a MOSFET 60 to transmit the input voltage V_IN to boost converter 56. In particular, the drain of MOSFET 60 is coupled to V_IN and the source of MOSFET 60 is coupled to input capacitor 68 and input inductor 70 of boost converter 56.

The gate of MOSFET 60 is coupled to a resistor divider formed by resistors 62, 64. Resistor 64 is coupled to a control signal, which may be the output of comparator 58 (FIG. 3). When comparator 58 indicates that the input voltage V_IN does not exceed the threshold voltage V_TH, the control signal goes high, thereby applying a bias to the gate of MOSFET 60 via resistor 62. Again, the threshold voltage may be on the order of approximately 2.4 to 2.6 volts, e.g., for two AAA cells. In response to the gate bias, MOSFET 60 turns "ON" and transmits the input voltage V_IN to boost converter 56.

When the comparator indicates that the input voltage V_IN exceeds the threshold voltage V_TH, however, the control signal goes low and turns MOSFET "OFF." In this case, boost converter 56 receives the input voltage V_IN less a diode drop, e.g., 0.6 volts, created by the body diode 66 of MOSFET 60. Hence, boost converter 56 receives a reduced input voltage (V_IN minus 0.6 volts), which should avoid pulse skipping. In operation, for example, if input voltage V_IN is 3.2 volts, MOSFET 60 will be turned off such that boost converter receives an input voltage of 3.2 volts minus 0.6 volts, i.e., 2.6 volts.

Figure 5:
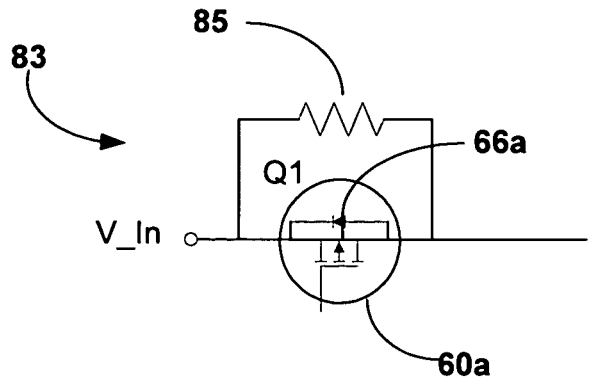
FIG. 5 is a circuit diagram illustrating an alternative input transistor configuration for the power management circuit of FIG. 4.

FIG. 5 is a circuit diagram illustrating an alternative input transistor configuration 83 for power management module 38 of FIG. 4. As shown in FIG. 5, input transistor configuration 83 may correspond substantially the input transistor configuration provided by MOSFET 60 in the example of FIG. 4. For example, configuration 83 includes a MOSFET 60a with body diode 66a. In addition, configuration 83 includes an external resistor 85 coupled across the source and drain of MOSFET 60. In this manner, MOSFET 60a transmits the input battery voltage V_IN, less a voltage drop across the resistor, to boost converter 56 when the transistor if OFF.

Figure 6:
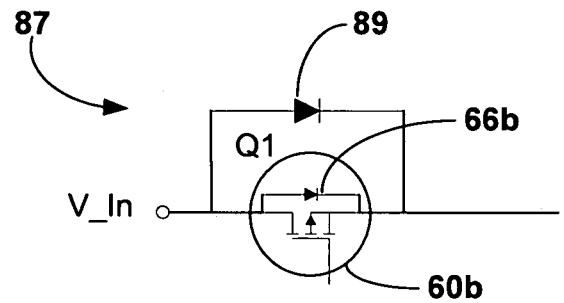
FIG. 6 is a circuit diagram illustrating another alternative input transistor configuration for the power management circuit of FIG. 4.

FIG. 6 is a circuit diagram illustrating another alternative input transistor configuration 87 for power management module 38 of FIG. 4. In the example of FIG. 6, configuration 87 includes a MOSFET 60b with body diode 66b, and an external diode 89 coupled across the drain and source of MOSFET 60b. In configuration 87, MOSFET 60b transmits the input battery voltage V_IN, less a diode drop on external diode 89, to the boost converter 56 when MOSFET 60b is OFF.

Figure 7:
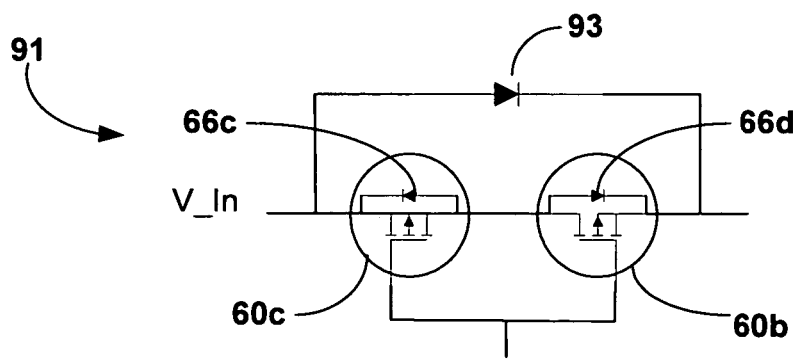
FIG. 7 is a circuit diagram illustrating a further alternative input transistor configuration for the power management circuit of FIG. 4.

FIG. 7 is a circuit diagram illustrating a further alternative input transistor configuration 91 for power management module 38 of FIG. 4. In the example of FIG. 7, configuration 91 includes a back-to-back MOSFET pair, including MOSFETs 60c, 60d with respective body diodes 66c, 66d. Configuration 91 further includes an external diode 93 coupled across the MOSFET pair. In configuration 92, MOSFETs 60c, 60d transmit the input battery voltage V_IN, less a diode drop on external diode 93, to boost converter 56 when MOSFETs 60c, 60d are turned OFF.

Figure 8:
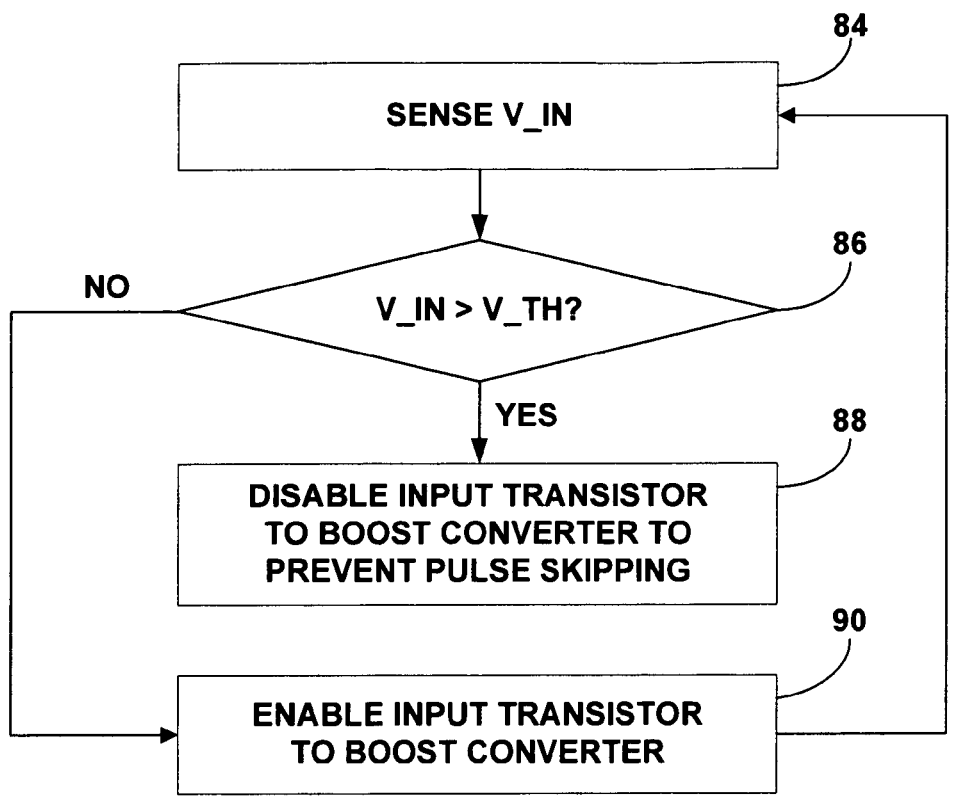
FIG. 8 is a flow diagram illustrating operation of the power management circuit of FIG. 4.

FIG. 8 is a flow diagram illustrating operation of the power management module 38 of FIG. 4. As shown in FIG. 8, power management module 38 senses the input voltage V_IN (84), compares the input voltage V_IN to a threshold voltage V_TH (86). More specifically, power management module 38 determines whether the input voltage V_IN is greater than (as indicated by ">" in FIG. 8) the threshold voltage V_TH. If the input voltage V_IN exceeds (i.e., is greater than) the threshold voltage V_TH, e.g., approximately 2.4 to 2.6 volts, power management module 38 disables an input transistor such as MOSFET 60 (FIG. 4) to reduce the input voltage and thereby prevent pulse skipping in boost converter 56 (88). If the input voltage V_IN does not exceed (i.e., is not greater than) the threshold voltage V_TH, power management module 38 enables the input transistor to transmit the input voltage V_IN to boost converter 56 (90).

Various embodiments of the invention have been described. However, one skilled in the art will appreciate that various additions and modifications can be made to these embodiments without departing from the scope of the invention. Although a neurostimulation programmer has been described herein for purposes of illustration, the invention may be generally applicable to any programmer useful with an implanted medical device, including patient programmers or physician programmers within the context of the clinical programming environment. The implantable medical device may provide stimulation therapies for pain and movement disorders and may include other stimulation-based therapies as well. Also, a programmer in accordance with the invention may be applicable to other implantable medical devices such as implantable drug delivery devices, and implantable cardiac pacemakers, cardioverters, or defibrillators, as well as non-implanted, external medical devices such as stimulators, drug pumps, or the like, and medical devices including both and external components. In addition, the invention is not limited to any particular implanted battery cell type, as AAA batteries have been described merely for purposes of illustration. These and other embodiments are within the scope of the following claims.

The invention claimed is:

1. A programmer for a medical device, the programmer comprising:
a wireless telemetry circuit adapted to communicate with the medical device;
a boost converter adapted to convert a battery voltage to an operating voltage for the programmer; and
a control circuit adapted to inhibit pulse skipping by the boost converter when a level of the battery voltage is greater than a threshold voltage,
wherein the control circuit includes a transistor coupled to transmit the battery voltage to the boost converter when the transistor is ON, wherein the transistor turns OFF when the battery voltage exceeds the threshold voltage.

2. The programmer of claim 1, wherein the control circuit includes a comparator to compare the battery voltage to the threshold voltage, wherein an output of the comparator is coupled to a gate of the transistor to turn the transistor ON and OFF based on the comparison.

3. The programmer of claim 1, wherein the transistor includes a MOSFET, and the transistor transmits the battery voltage, less a body diode drop of the MOSFET, to the boost converter when the transistor is OFF.

4. The programmer of claim 1, wherein the transistor includes a MOSFET, and the transistor transmits the battery voltage, less a resistor voltage drop, to the boost converter when the transistor is OFF.

5. The programmer of claim 1, wherein the transistor includes a MOSFET, and the transistor transmits the battery voltage, less an external diode drop, to the boost converter when the transistor is OFF.

6. The programmer of claim 1, wherein the transistor includes a back-to-back MOSFET pair having a first MOSFET and a second MOSFET, and the transistor transmits the battery voltage less an external diode drop, to the boost converter when each of the first and second MOSFETs is OFF.

7. A programmer for a medical device, the programmer comprising:
a wireless telemetry circuit adapted to communicate with the medical device;
a boost converter adapted to convert a battery voltage to an operating voltage for the programmer; and
a control circuit adapted to inhibit pulse skipping by the boost converter when a level of the battery voltage is greater than a threshold voltage,
wherein the control circuit inhibits pulse skipping by the boost converter by limiting the level of the battery voltage applied to the boost converter.

8. A method for controlling a power supply in a programmer for a medical device, the method comprising:
applying a battery voltage to a boost converter to convert the battery voltage to an operating voltage for the programmer;
inhibiting pulse skipping by the boost converter when a level of the battery voltage is greater than a threshold voltage; and
transmitting the battery voltage to the boost converter via a transistor, and turning the transistor OFF when the battery voltage exceeds the threshold voltage.

9. The method of claim 8, further comprising comparing the battery voltage to the threshold voltage with a comparator, wherein an output of the comparator is coupled to a gate of the transistor to turn the transistor ON and OFF based on the comparison.

10. The method of claim 8, wherein the transistor is a MOSFET, and the transistor transmits the battery voltage less a body diode drop of the MOSFET to the boost converter when the transistor is OFF.

11. The method of claim 8, wherein the transistor includes a MOSFET, and the transistor transmits the battery voltage, less a resistor voltage drop, to the boost converter when the transistor is OFF.

12. The method of claim 8, wherein the transistor includes a MOSFET, and the transistor transmits the battery voltage, less an external diode drop, to the boost converter when the transistor is OFF.

13. The method of claim 8, wherein the transistor includes a back-to-back MOSFET pair having a first MOSFET and a second MOSFET, and the transistor transmits the battery voltage less an external diode drop, to the boost converter when each of the first and second MOSFETs is OFF.

14. A method for controlling a power supply in a programmer for a medical device, the method comprising:
applying a battery voltage to a boost converter to convert the battery voltage to an operating voltage for the programmer; and
inhibiting pulse skipping by the boost converter when a level of the battery voltage is greater than a threshold voltage,
wherein inhibiting pulse skipping by the boost converter comprises limiting the level of the battery voltage applied to the boost converter.

15. A system for controlling a power supply in a programmer for a medical device, the system comprising:
means for applying a battery voltage to a boost converter to convert the battery voltage to an operating voltage for the programmer; and
means for inhibiting pulse skipping by the boost converter when a level of the battery voltage is greater than a threshold voltage,
wherein the battery voltage is transmitted to the boost converter via a transistor, the system further comprising means for turning the transistor OFF when the battery voltage exceeds the threshold voltage.

16. The system of claim 15, wherein the transistor is a MOSFET, and the transistor transmits the battery voltage less a body diode drop of the MOSFET to the boost converter when the transistor is OFF.

17. The system of claim 15, wherein the transistor includes a MOSFET, and the transistor transmits the battery voltage, less a resistor voltage drop, to the boost converter when the transistor is OFF.

18. The system of claim 15, wherein the transistor includes a MOSFET, and the transistor transmits the battery voltage, less an external diode drop, to the boost converter when the transistor is OFF.

19. The system of claim 15, wherein the transistor includes a back-to-back MOSFET pair having a first MOSFET and a second MOSFET, and the transistor transmits the battery voltage less an external diode drop, to the boost converter when each of the first and second MOSFETs is OFF.

20. A system for controlling a power supply in a programmer for a medical device, the system comprising:
means for applying a battery voltage to a boost converter to convert the battery voltage to an operating voltage for the programmer;
means for inhibiting pulse skipping by the boost converter when a level of the battery voltage is greater than a threshold voltage; and
means for inhibiting pulse skipping by the boost converter by limiting the level of the battery voltage applied to the boost converter.

21. A neurostimulation system comprising:
an implantable neurostimulator; and
a programmer for the neurostimulator, the programmer including a wireless
telemetry circuit adapted to communicate with the medical device, a boost converter adapted to convert a battery voltage to an operating voltage for the programmer, wherein the boost converter activates pulse skipping when the operating voltage exceeds a reference voltage, and the boost converter is a fixed-frequency switching mode boost converter, and a control circuit adapted to inhibit pulse skipping by the boost converter when a level of the battery voltage is greater than a threshold voltage,
wherein the control circuit is adapted to inhibit pulse skipping by the boost converter by limiting the level of the battery voltage applied to the boost converter.

22. A neurostimulation system comprising:
an implantable neurostimulator;
a programmer for the neurostimulator, the programmer including a wireless
telemetry circuit adapted to communicate with the medical device, a boost converter adapted to convert a battery voltage to an operating voltage for the programmer, wherein the boost converter activates pulse skipping when the operating voltage exceeds a reference voltage, and the boost converter is a fixed-frequency switching mode boost converter, and a control circuit adapted to inhibit pulse skipping by the boost converter when a level of the battery voltage is greater than a threshold voltage; and
a battery source to produce the battery voltage,
wherein the battery source includes two or more AAA battery cells, AA battery cells, C battery cells, or D battery cells.

23. A programmer for a medical device, the programmer comprising:
a wireless telemetry circuit configured to communicate with the medical device;
a fixed-frequency, switching mode boost converter configured to convert a battery voltage to an operating voltage for the programmer, wherein the boost converter performs pulse skipping when the operating voltage exceeds a reference voltage; and
a control circuit configured to limit a level of the battery voltage applied to the boost converter when the battery voltage exceeds a threshold voltage, thereby inhibiting performance of pulse skipping by the boost converter.

24. The programmer of claim 23, wherein the control circuit includes a transistor coupled to transmit the battery voltage to the boost converter when the transistor is ON, wherein the transistor turns OFF when the battery voltage exceeds the threshold voltage, and wherein the control circuit includes a comparator to compare the battery voltage to the threshold voltage, wherein an output of the comparator is coupled to a gate of the transistor to turn the transistor ON and OFF based on the comparison.

25. A method for controlling a power supply in a programmer for a medical device, the method comprising:
applying a battery voltage to a fixed-frequency, switching mode boost converter to convert the battery voltage to an operating voltage for the programmer, wherein the boost converter performs pulse skipping when the operating voltage exceeds a reference voltage; and
limiting a level of the battery voltage applied to the boost converter when the battery voltage exceeds a threshold voltage, thereby inhibiting performance of pulse skipping by the boost converter.

26. The method of claim 25, further comprising transmitting the battery voltage to the boost converter via a transistor when the transistor is ON, wherein limiting a level of the battery voltage applied to the boost converter comprises turning the transistor OFF when the battery voltage exceeds the threshold voltage.

27. A device for controlling a power supply in a programmer for a medical device, the device comprising:
means for applying a battery voltage to a fixed-frequency, switching mode boost converter to convert the battery voltage to an operating voltage for the programmer, wherein the boost converter performs pulse skipping when the operating voltage exceeds a reference voltage; and
means for limiting a level of the battery voltage applied to the boost converter when the battery voltage exceeds a threshold voltage, thereby inhibiting performance of pulse skipping by the boost converter.

28. The method of claim 27, further comprising means for transmitting the battery voltage to the boost converter via a transistor when the transistor is ON, wherein the means for limiting a level of the battery voltage applied to the boost converter comprises means for turning the transistor OFF when the battery voltage exceeds the threshold voltage.

29. A programmer for a medical device, the programmer comprising:
a wireless telemetry circuit adapted to communicate with the medical device;
a boost converter adapted to convert a battery voltage to an operating voltage for the programmer;
a control circuit adapted to inhibit pulse, skipping by the boost converter when a level of the battery voltage is greater than a threshold voltage; and
a comparator that compares the level of the battery voltage to the threshold voltage.

30. A method for controlling a power supply in a programmer for a medical device, the method comprising:
applying a battery voltage to a boost converter to convert the battery voltage to an operating voltage for the programmer;
inhibiting pulse skipping by the boost converter when a level of the battery voltage is greater than a threshold voltage; and
comparing the level of the battery voltage to the threshold voltage.

31. A system for controlling a power supply in a programmer for a medical device, the system comprising:
means for applying a battery voltage to a boost converter to convert the battery voltage to an operating voltage for the programmer;

means for inhibiting pulse skipping by the boost converter when a level of the battery voltage is greater than a threshold voltage; and means for comparing the level of the battery voltage to the threshold voltage.

32. A neurostimulation system comprising:

an implantable neurostimulator; and a programmer for the neurostimulator, the programmer including a wireless telemetry circuit adapted to communicate with the medical device, a boost converter adapted to convert a battery voltage to an operating voltage for the programmer, wherein the boost converter activates pulse skipping when the operating voltage exceeds a reference voltage, and the boost converter is a fixed-frequency switching mode boost converter, and a control circuit adapted to inhibit pulse skipping by the boost converter when a level of the battery voltage is greater than a threshold voltage, wherein the programmer comprises a comparator that compares the level of the battery voltage to the threshold voltage.

* * * * *